United States Patent [19]

Okamoto et al.

[11] 4,338,943
[45] Jul. 13, 1982

[54] INSTRUMENT FOR INDUCTION OF LABOR

[75] Inventors: Tadao Okamoto; Eisuke Obata, both of Tokyo; Yutaka Enomoto, Kawaguchi, all of Japan

[73] Assignee: Fuji Latex Co., Ltd., Tokyo, Japan

[21] Appl. No.: 236,068

[22] Filed: Feb. 19, 1981

Related U.S. Application Data

[62] Division of Ser. No. 38,908, May 14, 1979, Pat. No. 4,270,541.

[51] Int. Cl.³ .............................................. A61M 29/02
[52] U.S. Cl. ................................................... 128/344
[58] Field of Search .................... 128/344, 349 B, 246, 128/129

[56] References Cited

U.S. PATENT DOCUMENTS

| | | | |
|---|---|---|---|
| 901,376 | 10/1908 | Roberts | 128/344 X |
| 1,652,954 | 12/1927 | Pierce | 128/344 X |
| 1,690,995 | 11/1928 | Pratt | 128/344 |
| 2,026,747 | 1/1936 | Nemzek | 128/344 |
| 2,499,045 | 2/1950 | Walker et al. | 128/344 X |
| 2,541,520 | 2/1951 | Kegel | 128/344 X |
| 3,435,826 | 4/1969 | Fogarty | 128/344 X |
| 3,480,017 | 11/1969 | Shute | 128/344 |
| 3,900,033 | 8/1975 | Leininger et al. | 128/344 |

Primary Examiner—John D. Yasko
Attorney, Agent, or Firm—Kalish & Gilster

[57] ABSTRACT

An instrument for induction of labor comprising a tubular member or catheter being closed at its forward or leading end and open at its rearward or trailing end; there being an inflatable bag or balloon in enveloping relationship to the forward end portion of the catheter and being engaged in leak-proof manner thereto. At least one orifice is provided adjacent the forward end of the catheter within the bag for effecting communication between the said bag and the catheter for the introduction of liquid into the bag for inflating same to a predetermined extent dictated by the presentation of the fetus. A method for inducing labor comprising inserting into the uterus a liquid inflatable bag mounted upon the forward end portion of a tubular member with the bag being presented between the uterine wall and the amniotic membrane. Liquid is introduced into the bag for inflating of the same with the quantity of such liquid being dependent upon whether the fetus is in head or breech presentation, leaving the inflated bag in such position for promoting dilatation of the cervical opening and then effecting removal of said bag and tubular member for completion of the cervix dilatation.

6 Claims, 5 Drawing Figures

INSTRUMENT FOR INDUCTION OF LABOR

This is a Divisional application of Ser. No. 38,908 filed May 14, 1979 now U.S. Pat. No. 4,270,541.

BACKGROUND AND SUMMARY OF THE INVENTION

This invention relates in general to the field of obstetrics and, more particularly, to an instrument for induction of labor as well as a method for inducing labor.

Methods for induction of labor are divided into two primary categories, namely medical and mechanical. The particular method depends upon the condition or state of the involved organs with respect to delivery. The medical method would be the method of choice when the cervix is in a fully matured, loose condition and the uterus sensibility is heightened, or when the cervical orifice has dilated more than the width of two fingers. Only an intermittent intramuscular injection of posterior pituitary extract or an intravenous drip is adequate, in most cases, to assure a successful delivery. If with such conditions an artificial rupture of the amniotic membrane is effected, a more certain result can be obtained. However, when the cervix has not reached a state of maturity the medical method is not effective. Thus, to practice a medical method the particular organs must have reached a predetermined condition of potential delivery readiness. Without such even increased amounts of medication are insufficient to induce labor. Therefore, the medical method has recognized limitations and can only be used under certain conditions.

The mechanical method is employed when induction of labor is necessary in those situations wherein the particular organs have not reached the level of delivery readiness as would indicate resort to the medical method. Among the more well known mechanical methods are the Bougierung method, being the induction of an instrument for dilating constricted areas; metreurysis, being a dilatation of the uterine cervix with a metreurynter, and colpeurysis, involving a mechanical dilatation of the vagina. However, such methods have not in practice by any means proved infallible and thus the results obtained have been quite uncertain. In many cases resort has necessarily been made to cesarean section in an effort to save the child. It is commonly recognized that when the death rates of the full and frank presentation and the footling presentation are compared, the prognosis for a sound delivery is more unfavorable in the latter presentation. Such prognosis has heretofore led to the view that delivery of footling presentation, whether single or double, should preferably be effected by cesarean section. Despite the stages of development of both types of methods, medical and mechanical, certain types of birth have not proved reliable by either method.

Therefore, it is an object of the present invention to provide an instrument for inducing labor which is useful regardless of the presentation of the fetus thereby being productive of a diminution of the death rate with certain types of births which had been considered particularly hazardous heretofore.

It is another object of the present invention to provide an instrument of the character stated the use of which markedly reduces the heretofore accepted necessity to the resort to cesarean section.

It is a still further object of the present invention to provide an instrument of the character stated which has been extensively tested so that its effectiveness is established.

It is another object of the present invention to provide an instrument of the character stated which may be easily utilized by a practitioner with limited instruction.

It is a still further object of the present invention to provide a method for inducing labor which promotes a most substantial degree of sound deliveries without peril to the fetus despite the manner of presentation of the fetus.

It is a further object of the present invention to provide an instrument for the induction of labor which is not harmful to the mother and thus may be used with safety.

It is another object of the present invention to provide an instrument for the induction of labor which may be most economically manufactured; which is most durable in usage; and the practice of the same has promoted a level of reliability hitherto unknown through the performance of the customary medical and mechanical methods.

The present invention comprehends, in essence, a tubular body as a catheter type having an inflatable balloon or bag fixed on the normally forward or leading end of the catheter and enclosing the adjacent portion of the catheter which is provided with a port or orifice for discharge therethrough of a compatible liquid, such as, sterile saline solution, or even water, into the balloon for inflating same with a predetermined volume of such liquid dependent upon the presentation of the fetus. The instrument is inserted between the uterus wall and the amniotic membrane through the cervical orifice and after such insertion the liquid is gradually fed into the balloon through the catheter portion to a predetermined limit if there is head presentation to avoid the danger of prolapse of the umbilical cord or the possibility of a change of position of the fetus. In the event there is a breech presentation, the amount of liquid introduced into the balloon is in greater amount for purposes presently appearing. At the appropriate juncture the instrument is automatically removed by dropping through the cervical orifice.

DESCRIPTION OF PRACTICAL EMBODIMENTS

Figure 1:
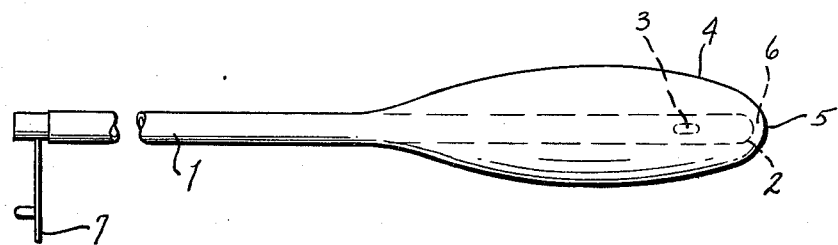
FIG. 1 is a side view of an instrument for the induction of labor constructed in accordance with and embodying the present invention.

Referring now by reference numerals to the drawings which illustrate practical embodiments of the present invention, 1 indicates a catheter or tubular member being closed at its normally forward or leading end and being provided with one or more ports or orifices 3 adjacent to but spaced from the forward end extremity 2. Said catheter 1 may be molded of any suitable flexible and durable material, such as, soft synthetic resin, natural or synthetic rubber or the like. Enclosing the forward end portion of catheter 1 is a relatively thin walled balloon or inflatable bag 4 fabricated as of natural or synthetic rubber and being suitably sealed at its rearward or trailing end, such as by means of a pouch with the outer wall of catheter 1 so as to render the joint therebetween leakproof. It will be seen that openings 3 are within balloon 4 so that liquid fed through catheter 1 will be received within said balloon. Balloon 4 is of such size that its forward end 5 is spacedly forwardly of extremity 2 of catheter 1 so as to cause the development of a limited spacing 6 therebetween so that other than the sealing of balloon 4 to catheter 1, as above described, there is no engagement therebetween. At its rearward end or trailing extremity, catheter 1 is provided with a removable plug 7.

The instrument of the present invention is preferably utilized after the practitioner has determined that the cervix is mature for delivery. There are three critical points to indicate the degree of cervical maturation, namely the extent of cervix effacement, the degree of dilatation of the cervical orifice, and the degree of softness of the cervix. Thus, with the present instrument it is requisite to confirm that the cervix effaces more than 50 percent; that the cervical orifice has dilated to a width greater than two centimeters, and that the cervix is soft. Disregard of these conditions in that the instrument is utilized before the requisite level of maturity has been reached could result not only in the delay of delivery, but also that the delivery progresses with the cervical orifice in a nonfully dilated state even after the instrument has dropped through the cervical orifice. With the cervical orifice not fully dilated, extraction of the head, as well as assisted delivery of the shoulder and arms, is difficult to carry out.

Figure 5:
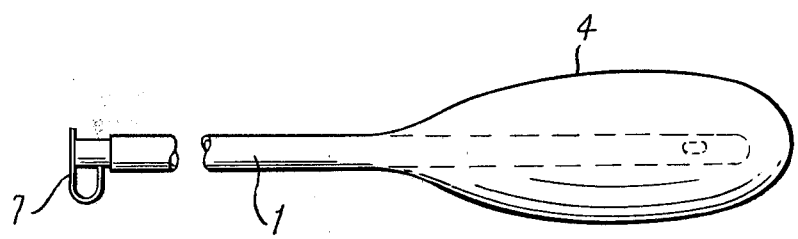
FIG. 5 is a side view of the instrument illustrated in FIG. 1 but showing the balloon in expanded state.

The instrument, after sterilization through boiling, in inserted by the doctor between the uterine wall and the amniotic membrane through the cervical orifice is substantially the same manner as Bougierung. In the act of insertion the doctor places the leading extremity 2 of the catheter 1 at the cervical orifice holding the balloon 4 and then inserts catheter 1 moving his fingers backwardly until he senses that the instrument has been inserted to a desired extent. Thereafter, with plug 7 removed the doctor then pours into the rearwardly open end of catheter 1 on a gradual basis a suitable liquid, such as, sterile saline solution, for flow into balloon 4 via openings 3, as by means of a 100 g injector. In the case of head presentation of the fetus, 300 cc–350 cc of the solution is introduced into the balloon 4 causing expansion of the same as generally illustrated in FIG. 5. The rearward end of catheter 1 is then closed by reinsertion of plug 7 and the rearward portion of catheter 1 is coiled in the vagina. Any traction by a weight is not utilized. As indicated above, the limitation of the injection to no more than 350 cc in the case of head presentation is to avoid a danger of prolapse of the umbilical cord or shoulders and arms, or difficulties which might arise through a change of the fetal position. In the event that the fetus is breech presented, then more than 400 cc of the sterile saline solution is injected into the balloon 4 with consequent commensurate expansion of the same.

After insertion of the instrument of the present invention labor commences in about one hour on average. The cervical orifice dilates almost completely in 7 to 8 hours in the case of a primipara, and in 4 to 5 hours in the case of a multipara. Upon such dilation the instrument of the present invention will drop through the cervical orifice and into the vagina for facile removal. At this particular stage labor becomes weak for a limited interval so that after an internal examination the instrument is removed. If the labor continues weak, a citravenous drip of oxytoxin is given to the pregnant woman. If the labor grows strong again, an artificial rupture of the amniotic membrane is performed after full confirmance of the complete dilation of the cervical orifice. Thereafter delivery proceeds rapidly.

The instrument of the present invention can thus induce labor most effectively. Eighty instances of employment of the present instrument has demonstrated that its use has seldom any ill effect and that it could achieve the intended purpose even in those cases where medicine was incapable of inducing labor. The instrument of this invention can be used most efficaciously as a mechanical method for delivery in the last stage of pregnancy and has been often employed in cases of breech presentation, especially of footling presentation, which is one of the greatest causes of infant death during pregnancy. The prognosis of successful birth in footling presentation has been found most favorable if no premature rupture of the membrane has taken place, and the cervical orifice has fully dilated. If the method of this invention is applied at the appropriate juncture the prognosis as to birth is substantially the same as in the case of full and frank presentation thereby obviating the heretofore customary resort to cesarean section; but with the proviso that no joint disease is present. Thus, the use of the present instrument makes it possible to perform a planned delivery of footling presentation with remarkably decreased possibility of infant death. Actually, the utilization of the present instrument greatly diminishes most of the heretofore accepted risks in delivery of breech presentation, such as through prolapse of the umbilical cord and the difficulty in extracting the fetal head before complete dilation of the cervical orifice. Thus, by the present invention, in footling presentations, full dilation of the cervical orifice and the soft parturient canal is substantially effected, with the greatest advantage being the facilitation of an assisted delivery of shoulder and arms and withdrawal of the following head. Additionally, the use of this invention can prevent a premature rupture of the membrane as well as a premature prolapse of the umbilical cord. A further advantage resides in the fact that it makes a planned delivery possible so that delivery can be effected even while a hospital is in a highly active state with extreme demands upon its personnel.

Thus, the present method as practiced in conjunction with breech presentation involves the dilation of the cervical orifice almost completely; requiring induction of about 500 ml of sterile solution into the balloon 4. A general type of metreurysis as heretofore known is inadequate to bring about the foregoing results.

Without the use of the instrument of the present invention the prolapse of the umbilical cord which often accompanies the footling presentation, especially in a primipara, will inevitably require a cesarean section.

Figure 2:
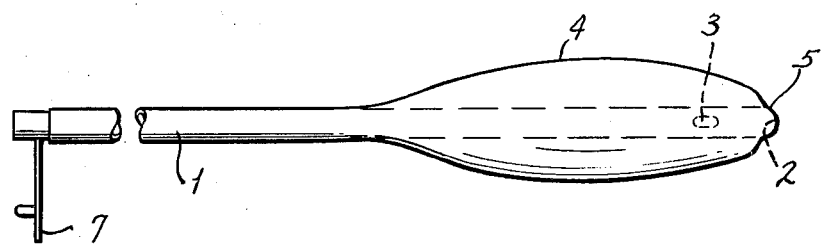
FIG. 2 is a side view of another form of instrument for induction of labor constructed in accordance with and embodying the present invention.
Figure 3:
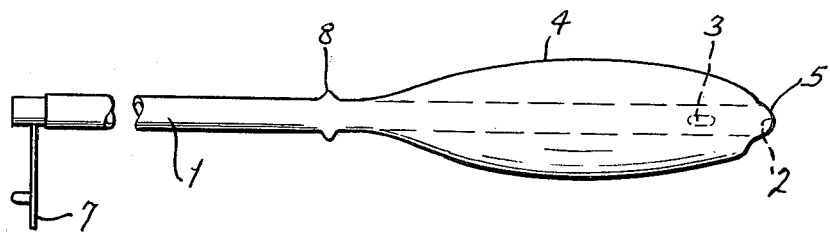
FIG. 3 is a side view of a further form of instrument for induction of labor constructed in accordance with and embodying the present invention.
Figure 4:
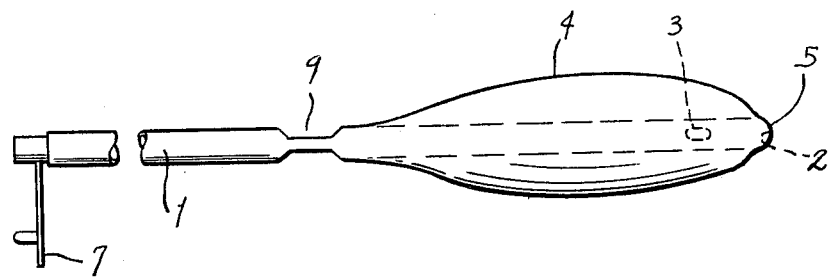
FIG. 4 is a side view of a still further form of instrument for induction of labor constructed in accordance with and embodying the present invention.

Turning now to FIG. 2, another form of instrument for induction of labor is shown wherein like components as those incorporated within the instrument shown in FIG. 1 are identified by like reference numerals for purposes of brevity. The difference between the structure shown in FIG. 2 and that shown in FIG. 1 is that the former is devoid of the spacing 6 so that the front end extremity 2 of catheter 1 is pressed tightly into the adjacent portion of balloon 4. With the use of the instrument shown in FIG. 2, as the same is inserted into the cervical canal by the practitioner's fingers, the engaged end extremity 2 and the confronting portion of balloon 4 will move together so that during such travel ballon 4 can be inserted into the cervical canal without any relative or irregular movement between catheter 1 and balloon 4. With the structure of FIG. 1 the spacing 6 manifestly denies a snug joint between catheter 1 and balloon 4 so that the latter is prone to be inserted in a biased fashion into the cervical canal as the doctor guides same with his fingers and to thus be expanded as in an asymmetrical manner with respect to catheter 1 as the sterile saline solution is introduced into balloon 4 through openings 3. Thus, the form of the instrument shown in FIG. 2 overcomes, in practice, the possibility of balloon 4 being expanded in asymmetrical fashion with respect to catheter 1. In most conditions this difference would not be significant but in certain conditions it is preferable that the balloon 4 when being inserted into the cervical canal be in a symmetrical state as shown in FIG. 2 so that no unnecessary pain might be caused the patient. By this form of the instrument a doctor may perform delivery with a more reliable technique as the condition merits.

The efficacy of the instrument of the present invention and of the method for inducing labor, as above described, may best be understood by resort to the following which sets forth results, in substantially tabulated form, of actual clinical investigation.

(1) Rate of Effectiveness:

The ideal use of the present instrument is in dilating the cervical orifice to such a degree that the fetus can be delivered in a natural state. Of the 313 cases shown in Table 1, 12 cases were not considered fully successful. These omitted cases comprise one abdominal cesarean section due to the rigidity of the cervical orifice (a primipara of 38 year old woman), nine uterus orifice incisions and two craniotomies. Excluding the abdominal cesarean section which was performed as a test delivery considering the possibility that the rigidity of the cervical orifice loosened rapidly after the beginning of labor, six of nine cases of the cervical orifice incision were performed for breech presentation, especially for footling presentation. The craniotomies were performed to lessen the pain of pregnant women, whose fetus had died while in the uterus. These cases cannot necessarily be said to have been unsuccessful. It can be said that the desired purpose of the instrument was achieved as it helped dilate the cervical orifice to such an extent that those treatments could be given. As seen from Table 1, the rates of success were 100%, 100% and 96.1%, respectively, in deliveries of 8 months, 9 months, and 10 months.

TABLE 1

| | Rate of Effectiveness | | |
|---|---|---|---|
| Month of Pregnancy | Number of Cases | Success | Rate of Effectiveness |
| VIII | 3 | 3 | 100 |
| IX | 5 | 5 | 100 |
| X | 305 | 293 | 96.1 |

(2) Indications:

Table 2 shows ninety-five cases of cephalopelvic disproportions (47.5% of head presentations), including postmature infants and contracted pelvises, which were expected to make the delivery through a vaginal route impossible if the infants heads grew larger, thirty-three cases of premature rupture of the membrane which were not ready for delivery or to which a medical method was not effective; twenty-six cases of toxemias of pregnancy; twenty-two cases of so-called "postponement of the expected date" in accordance with the wish of pregnant women (however, delivery operation should not be done before the conditions for delivery are perfect); fourteen cases of social adaptations (for example, for women who live far from the hospital and are not in time for a hospital treatment after the labor has begun or who have already experienced a precipitate labor); four cases of hydraminios; three cases of death of infant while in the uterus and each one case of twins, hemicephalus and hydrocepharus.

All the above cases, except the postponements of the expected date are those in which the cervix had not shortened and the cervical orifice had dilated only one finger wide, and there was no hope for a natural labor for a while without giving any treatment and a medical method was believed to be incapable of inducing labor.

TABLE 2

| Indications | | |
|---|---|---|
| Cephalopelvic Disproportion | | 95 |
| Premature Rupture | | 33 |
| Toxemias of Pregnancy | | 26 |
| Postponement of the Expected Date | | 22 |
| Social Adaptations | | 14 |
| Hydramnios | | 4 |
| Death While in the Uterus | | 3 |
| Others: | | |
| Twins | | 1 |
| Hemicephalus | | 1 |
| Hydrocephalus | | 1 |
| Breech Presentations: | | |
| full and frank presentation | 71 | |
| footling presentation | 42 | 113 |
| TOTAL | | 313 |

The above breech presentations consist of seventy-one cases of full and frank breech presentations and forty-two cases of footling presentation. In recent years, the inventors' hospital has applied the present instrument to cases of breech presentation, in particular to those cases of footling presentation. The chief cause of the death of an infant in breech presentation in said hospital has been footling presentation. The footling presentation is apt to cause a premature rupture of the membrane by which the small parts of an infant descend before the cervical orifice has dilated fully and it makes it impossible to deliver the following head. That is the greatest reason why the footling presentation brings about the death of an infant. It has been found that the instrument for induction of labor according to the present invention can prevent the infant death due to the footling presentation. The present instrument, when inserted into the cervical canal not only helps induce labor but also works as a bag of water to prevent premature rupture of membrane and also the prolapse of foot portions. Because the cervical orifice dilates almost completely when the instrument drops from it, the later delivery can proceed easily. Indeed, the rate of death due to to footling presentation decreased remarkably after the present instrument was introduced. More particularly, there has been no death due to the footling presentation for the last three years.

In nine cases of full and frank breech presentations, the fetal position, which was in footling presentation when the instrument was inserted, changed into complete breech presentation. This fact demonstrates an important advantage of the use of the present instrument.

(3) The Number of Times of Child-Birth and the Time Required for Delivery:

The present instrument was applied to three hundred and five delivery cases of ten-month pregnant women. Excepting fifteen abdominal cesarean sections, nine cervical orifice incisions and two craniotomies, the remaining two hundred and seventy-nine cases consist of one hundred and sixty-five cases of primiparae and one hundred and fourteen cases of multiparae. In the former cases the time required to cause labor after insertion of the present instrument was 3 hours and 19 minutes. In the latter cases, it was 3 hours and 46 minutes.

However, the time required for delivery is as shown in Table 3. In the case of head presentation, the primiparae required 12 hours and 27 minutes, and multiparae 6 hours and 58 minutes. In the case of breech presentation, the primiparae required 9 hours and 30 minutes, and the multiparae 6 hours and 3 minutes. These figures show that each time for delivery, when the present instrument was used, is shorter than the time required for delivery after natural labor. In the case of natural labor, the head presentation and the breech presentation are little different in the time required for delivery, but, when the present instrument is used, the head presentation delivery requires less time. That is probably because of the greater amount of sterile saline solution that should be introduced into the balloon in the case of breech presentation.

TABLE 3

| | | Time Required for Delivery | |
|---|---|---|---|
| PRESENTATION | PRIMIPARA of MULTIPARA | NATURAL LABOR | THE PRESENT INSTRUMENT |
| Head | Primipara | 16 hours 30 minutes | 12 hours 27 minutes |
| | Multipara | 10 hours 42 minutes | 6 hours 58 minutes |
| Breech | Primipara | 16 hours 12 minutes | 9 hours 30 minutes |
| | Multipara | 10 hours  0 minutes | 6 hours  3 minutes |

(4) Joint-Use of Posterior Pituitary Hormone and an Artifical Rupture of the Membrane:

As labor becomes weak after the instrument has dropped into the vagina, posterior pituitary hormone and an artificial rupture of the membrane are often used together.

Table 4 shows whether or not other treatments were jointly given in one hundred and eighty-two cases of head presentation and one hundred and eight cases of breech presentation. The cases of abdominal cesarean section are omitted.

TABLE 4

| | Posterior Pituitary Hormone and An Artificial Rupture of the Membrane | | | |
|---|---|---|---|---|
| | Premature Rupture of the Membrane | Natural Rupture of the Membrane After the Instrument Has Dropped Out of the Cervical Canal | Artificial Rupture of the Membrane After the Instrument has Dropped Out of the Cervical Canal | Total |
| | HEAD PRESENTATION | | | |
| Intermittent Cutaneous Injection | 13 | 12 | 51 | 76 |
| Intravenous Drip | 7 | 6 | 30 | 43 | 119(65.4%) |
| No Injection | 12 | 9 | 12 | 63 | (31.6%) |
| TOTAL: | 32 | 27 | 123 | 182 |
| | BREECH PRESENTATION | | | |
| Intermittent Cutaneous Injection | 5 | 16 | 21 | 42 |
| Intravenous Drip | 5 | 16 | 9 | 30 | 72(66.7%) |
| No Injection | 7 | 14 | 15 | 36 | (33.3%) |
| TOTAL | 17 | 46 | 45 | 108 |

As seen from the above table, in the case of head presentation, the intermittent cutaneous injection of atonine 0 was applied to seventy-six cases and the intravenous drip to forty-three cases (total 119 cases, 65.4%); in the case of breech presentation, the intermittent cutaneous injection to forty-two cases and the intravenous drip to thirty cases (total 72 cases, 66.7%). The artificial rupture of the membrane was, in the case of head presentation, applied to one hundred and twenty-three cases (82.0%) in one hundred and fifty cases except the cases of premature rupture of the membrane; and, in the case of breech presentation, it was applied to forty-five cases (49.5%) in ninety-one cases. It can be said that the artificial rupture of the membrane is applied to nearly every case of head presentation after the present instrument has dropped into the vagina. Such results since the artificial rupture of the membrane maintains the fetus' head stable and the fore part of the instrument provides mechanical stimuli directly to the lower part of the uterus to promote labor and also serves to prevent prolapse of the umbilical cord or shoulder and arms. However, the artificial rupture of the membrane is not used as often in breech presentation as in head presentation, since, though in the cases of full and frank breech presentations, the membrane is ruptured as in head presentation, it is preferable to await a natural rupture of the membrane as long as possible in the case of footling presentation if only a little of the cervical orifice edge remains.

(5) Treatments Required After the Instrument Has Dropped From the Cervical Canal:

As shown in Table 5, cesarean section was performed in eleven cases (5.7%) among all the cases of head presentation. Eight such cases were of cephalopelvic disproportion, in which delivery through the vaginal route was considered impossible in view of the results of test delivery. The remaining three cases were, respectively, of a placenta previa, face presentation, and an eye disease (with danger of loss of sight in one eye and detached retina of the other eye). In the case of breech presentation, cesarean section was performed in four cases; two cases of which were contracted pelvis and one was of a postmature infant with the remaining one being of rigidity of the cervical orifice (primipara of a 38 year old woman).

TABLE 5

Treatments After the Instrument Has Dropped From the Cervical Canal

| HEAD PRE-SENTATION (193 Cases) | | BREECH PRE-SENTATION (112 Cases) | |
|---|---|---|---|
| Cesarean Section | 11(5.7%) | Cesarean Section After-Coming Head | 4(3.6%) |
| Forceps-Operation | 7(3.6%) | Forceps | 5(4.5%) |
| Vacuum-Extraction | 16(8.3%) | Vacuum-Extraction of the Coxae | 4(3.6%) |
| Craniotomy | 2(1.0%) | | |
| Incision of Cervical Orifice | 3(1.6%) | Incision of Cervical Orifice | 6(5.4%) |

Next, in the head presentation cases, forceps, vacuum extraction and craniotomy were used, respectively, with the percentages of 3.6%, 8.3% and 1.0%.

Incision of the cervical orifice was effected in 1.6% of the head presentation cases and in 5.4% of the breech presentation cases. In the latter cases, the operation was performed in almost every footling presentation. It is to be expected, in the case of footling presentation, that the problem will be solved by introducing a greater amount of sterile saline solution into the balloon.

(6) Unsuccessful Births:

As the conditions of each presentation are different, there have been certain situations wherein the use of the present instrument and the method of use were unsuccessful.

TABLE 6

| | Unsuccessful Births | | |
|---|---|---|---|
| | Present Instrument | Head Presentation | Breech Presentation |
| Rate of Infant Death | 3.0% | 7 (3.7%) | 2 (1.8%) |
| Prolapse of the Umbilical Cord | 4.6% | 8 (4.1%) | 6 (3.1%) |
| Prolapse of Shoulder and Arms | 1.3% | 3 (1.5%) | |
| Fever | 0.3% | 1 (0.5%) | 0 |
| Change of Infant Position (Shoulder Presentation) | 0 | 0 | 0 |

TABLE 6-continued

| | Unsuccessful Births | | |
|---|---|---|---|
| | Present Instrument | Head Presentation | Breech Presentation |

The number of cases of infant death when efforts were made to use the present instrument totaled nine (3%) in 301 cases of 10-month pregnancy, except four cases including two deaths while in the uterus, one hydrocephalus and one hemicephalus. In the nine cases, head presentation formed 3.7% and breech presentation 1.8%, and consisted of four cases of prolapse of the umbilical cord, two cases of breech presentation, two cases of hemorrhage in cranium and one case of lacenta dysfunction syndrome.

A total of eight cases (4.1%) of prolapse of the umbilical cord and three cases (1.5%) of prolapse of shoulder and arms were encountered in one hundred and ninety-three cases of head presentation. When the instrument according to the present invention was first used, the amount of sterile saline solution poured into the balloon was limited to about 300–350 cc. The results in eighty cases at that time showed no prolapse of the umbilical cord or shoulder and arms. Later on, in order to shorten the time for delivery, the amount of solution was increased to 400 cc, and with such amount, in head presentation, prolapse of the umbilical cord or shoulder and arms became relatively more frequent. At the present time, the amount is limited to 350 cc in the case of head presentation. As it is possible to conjecture the time the balloon drops from the cervical orifice because the labor, which has been strong, becomes weak rapidly, the balloon is then removed before it would be expelled from the vagina and the fetal head is maintained stable by means of artificial rupture of the membrane after confirming whether the umbilical cord or shoulder and arms prolapse or not. Even if prolapse is found, it is quite easy to return such to their correct position at this stage.

There were four infant deaths in eight cases of prolapse of the umbilical cord in head presentation. In each of the four cases, premature rupture of the membrane took place. In most cases of premature rupture of the membrane, labor does not become weak when the balloon drops from the cervical canal into the vagina and the fetal head falls into the breech. This often causes a doctor to fail to find the prolapse of the umbilical cord. It is not seldom that he doesn't notice it until the heart sound of an infant has stopped. So the present instrument should be applied to the cases of premature rupture of the membrane only when a medical method is not effective, and the amount of sterile saline solution to be introduced into the balloon should be no more than 300 cc. Further a doctor should do an internal examination frequently to be able to find the prolapse of the umbilical cord without fail.

In the case of breech presentation, prolapse of the umbilical cord was found in six cases (3.1%) in 112 cases. More particularly, it was found in two cases of complete presentation and in four cases of footling presentation. The cause of the prolapse of the cord in those cases did not necessarily result from the method of using the present invention as such can be seen from the fact that there were no infant deaths.

Fever of the mother due to infection was seen in one case (0.3%) in three hundred and five cases. The rate was very low, and the fever abated after delivery. Further, no change of an infant position was caused by the use of the instrument of the present invention.

Having described our invention, what we claim and desire to obtain by Letters Patent is:

1. An obstetrical instrument for induction of labor comprising an elongated, tubular member formed of flexible, durable, and soft material and having a leading end and a trailing end, said tubular member being closed at the extremity of its leading end and being opened at its trailing end, a relatively thin walled balloon fabricated of natural or synthetic rubber being disposed enclosingly about the leading end portion of said tubular member, said balloon being sealed in its rearward or trailing end portion about the outer face of said tubular member for development of a liquid leakproof joint therebetween, said joint being remote from the trailing end of said tubular member so that the latter between said joint and the trailing end thereof is fully exposed, said tubular member being provided with at least one opening adjacent its leading end for establishing communication between the interior of said tubular member and the interior of said inflatable balloon for permitting ingress into said balloon, and egress therefrom, of a compatible fluid for inflation of said balloon, said balloon being fabricated of fluid impervious material so that inadvertent loss of said fluid therefrom is inhibited, said tubular member and associated inflatable balloon being coordinatingly dimensioned for disposition between the uterine wall and the amniotic membrane whereby upon inflation of said balloon the uterine wall is stimulated with increase of internal pressure for promoting removal of the amniotic membrane, said tubular member being of such length in the direction of its trailing end from the balloon seal to permit introduction of the balloon through the cervical orifice and into the uterus.

2. An obstetrical instrument for induction of labor as defined in claim 1 and further characterized by the leading end of said tubular member being spaced a predetermined distance from the confronting portion of said inflatable balloon.

3. An obstetrical instrument for induction of labor as defined in claim 1 and further characterized by the leading end of said tubular member being in snug abutment against the confronting portion of said inflatable balloon.

4. An obstetrical instrument for induction of labor as defined in claim 1 and further characterized by indicator means provided on said tubular member between the trailing end thereof and said inflatable balloon.

5. An obstetrical instrument for induction of labor as defined in claim 4 and further characterized by said indicator means comprising an annular projection.

6. An obstetrical instrument for induction of labor as defined in claim 4 and further characterized by said indicator means comprising an annular depression.

* * * * *